United States Patent
Lee et al.

(10) Patent No.: US 8,866,622 B2
(45) Date of Patent: Oct. 21, 2014

(54) SYSTEM AND METHOD FOR PREVENTING DROWSINESS

(75) Inventors: Sang-Yub Lee, Yongin-Si (KR); Hyo-Sub Choi, Wanju-Gun (KR); Chul-Dong Lee, Seongnam-Si (KR); Sang-Hyun Park, Yongin-Si (KR)

(73) Assignee: Korean Electronics Technology Institute, Seongnam-si (KR)

( * ) Notice: Subject to any disclaimer, the term of this patent is extended or adjusted under 35 U.S.C. 154(b) by 399 days.

(21) Appl. No.: 13/308,759

(22) Filed: Dec. 1, 2011

(65) Prior Publication Data

US 2012/0139733 A1 Jun. 7, 2012

(30) Foreign Application Priority Data

Dec. 3, 2010 (KR) .................. 10-2010-0122628

(51) Int. Cl.
| | |
|---|---|
| *G08B 23/00* | (2006.01) |
| *A61B 5/00* | (2006.01) |
| *B60K 28/06* | (2006.01) |
| *A61B 5/18* | (2006.01) |
| *G08B 21/06* | (2006.01) |
| *A61B 5/0476* | (2006.01) |

(52) U.S. Cl.
CPC ............ *G08B 21/06* (2013.01); *A61B 5/6835* (2013.01); *A61B 5/0476* (2013.01); *A61B 5/6893* (2013.01); *B60K 28/066* (2013.01); *A61B 5/18* (2013.01)
USPC .......................... 340/575; 600/300; 600/383

(58) Field of Classification Search
CPC .................................. G08B 21/06; A61B 5/11
See application file for complete search history.

(56) References Cited

U.S. PATENT DOCUMENTS

2011/0028798 A1* 2/2011 Hyde et al. .................... 600/300
2011/0295127 A1* 12/2011 Sandler et al. ................ 600/484

FOREIGN PATENT DOCUMENTS

| JP | 2002-056500 A | 2/2002 |
|---|---|---|
| JP | 2010-019708 A | 1/2010 |

OTHER PUBLICATIONS

Korean Patent Office, Korean Office Action issued in corresponding KR Application No. 10-2010-0122628, dated Aug. 6, 2012.

* cited by examiner

*Primary Examiner* — Steven Lim
*Assistant Examiner* — Omeed Alizada
(74) *Attorney, Agent, or Firm* — Sughrue Mion, PLLC

(57) ABSTRACT

A system and a method for preventing drowsiness are provided. The system for preventing drowsiness calculates brainwaves of a user by receiving a signal around a head of a user without contact, detects a state of the user based on the calculated brainwaves, and performs a necessary function according to the detected state of the user. Thus, convenience is increased when measuring the brainwaves of the driver using the contactless electrodes.

9 Claims, 6 Drawing Sheets

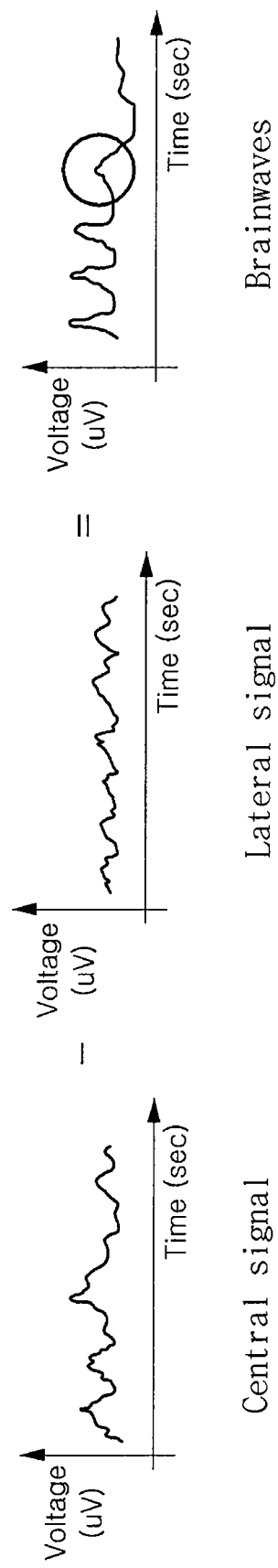

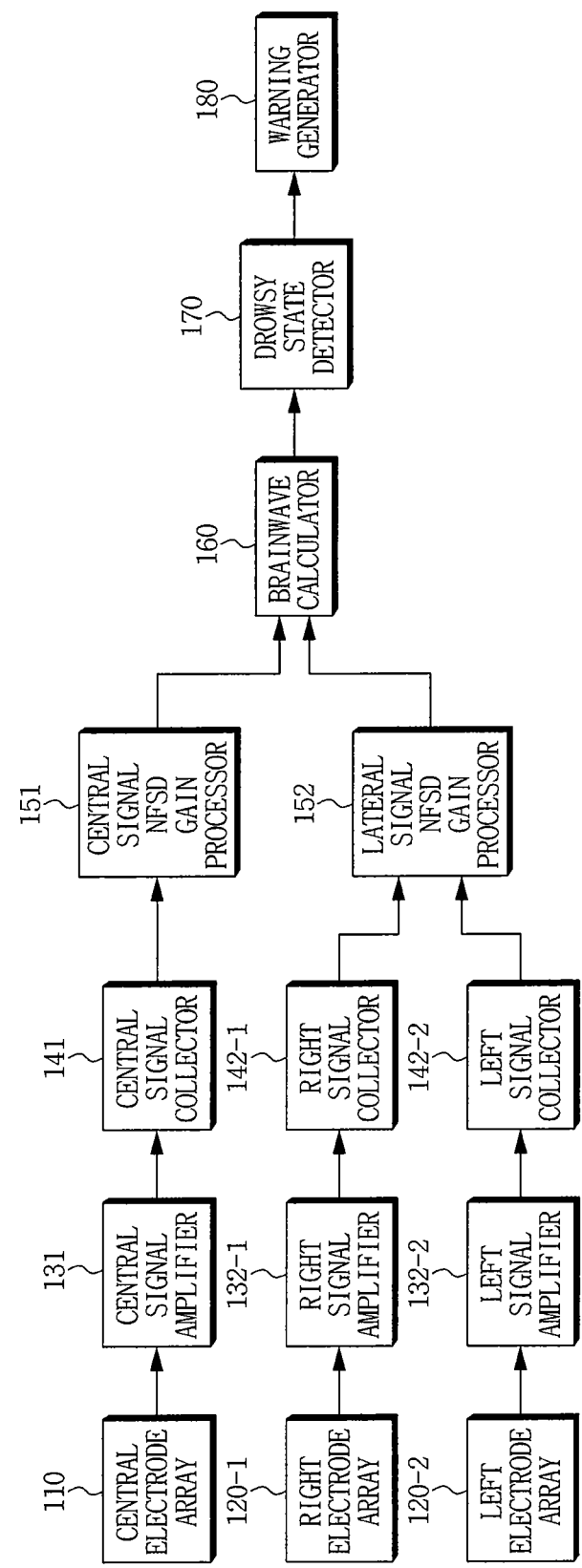

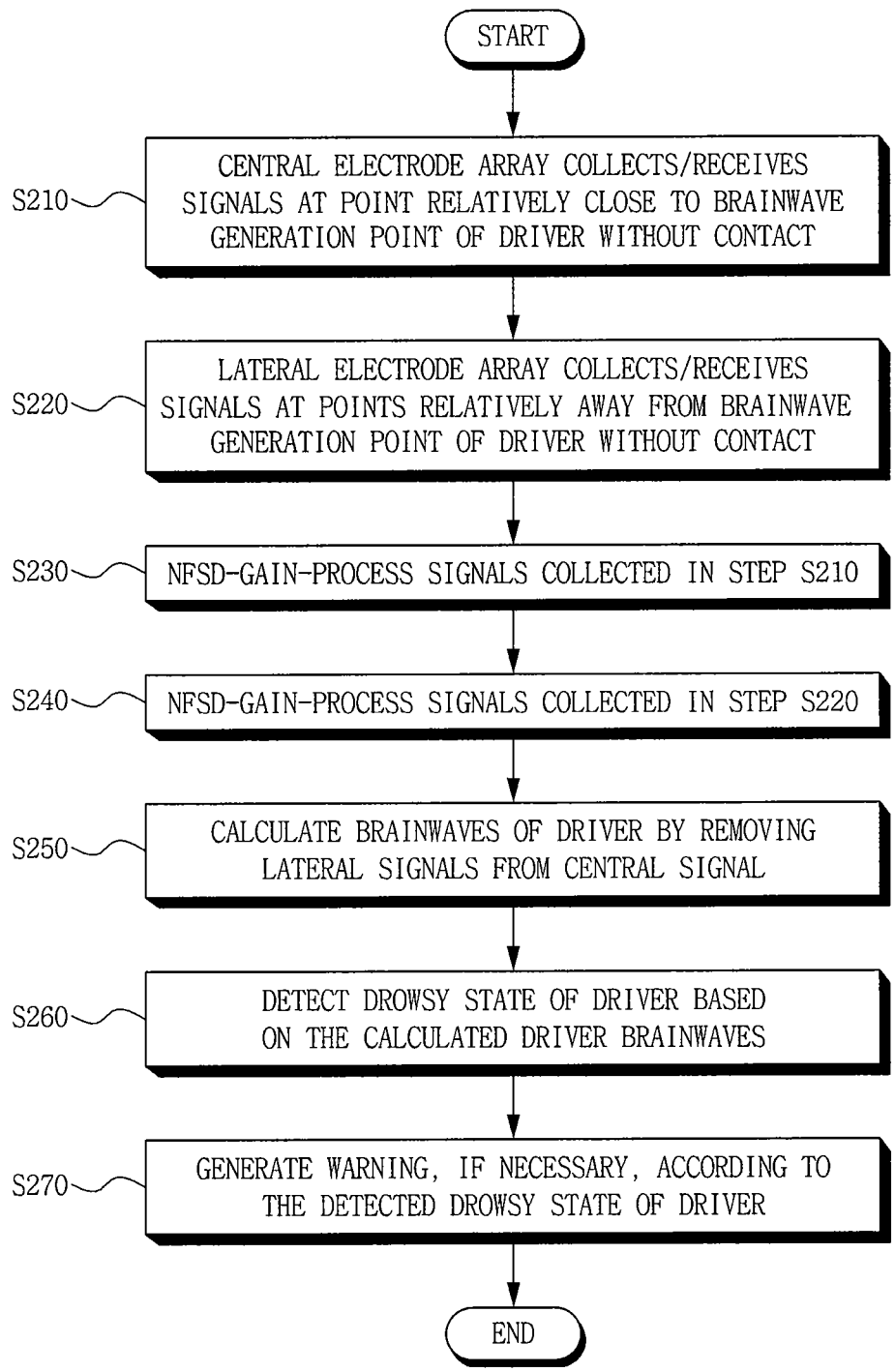

FIG. 6

| frequency | | brainwaves | | consciousness | |
|---|---|---|---|---|---|
| over 30Hz | | gamma wave | | outer consciousness | anxiety, agitation |
| 14~30Hz | | beta wave | | outer consciousness | working under strain in accordance with normal brainwave outside world |
| 8~14Hz | 12~13Hz | alpha waves | fast alpha | inner consciousness | concentration and some tension |
| | 10~12Hz | | middle alpha | | academic ability enhancement, mental concentration, maximum memory and concentration abilities, and stress relief |
| | 8~9Hz | | slow alpha | | meditation, impassive meditation |
| 4~7Hz | | theta wave | | inner consciousness | drowsiness, light sleep, brainwave when psychic power is used |
| 0.5~4Hz | | delta wave | | unconsciousness | deep sleep |

SYSTEM AND METHOD FOR PREVENTING DROWSINESS

CROSS-REFERENCE TO RELATED APPLICATION(S) AND CLAIM OF PRIORITY

The present application claims the benefit under 35 U.S.C. §119(a) to a Korean patent application filed in the Korean Intellectual Property Office on Dec. 3, 2010, and assigned Serial No. 10-2010-0122628, the entire disclosure of which is hereby incorporated by reference.

TECHNICAL FIELD OF THE INVENTION

The present invention relates generally to a system and a method for preventing drowsiness. More particularly, the present invention relates to a system and a method for preventing drowsiness when a dangerous accident can be caused by drowsiness as in driving.

BACKGROUND OF THE INVENTION

Most of existing driver drowsiness preventing systems recognize a drowsy state by detecting state of a pupil through driver face recognition, or recognizes the drowsy state based on a respiration pattern according to respiration of the driver.

However, using brainwaves, a contact device for measuring the brainwaves is used. The contact device can be problematic because its attachment causes uneasiness.

Meanwhile, a method estimates an eye blink interval through a brainwave signal. When reversely estimating the eye blink using the brainwaves, error can occur according to a noise signal, and an accident prevention rate lowers as an estimation process gets longer.

When the state of the pupil is detected through the driver face recognition, an algorithm for detecting the pupil state using an image input from a camera is very complex. When the external strong light comes into the camera, error is generated. Many errors arise according to the degree of the pupil and a head location of the driver per person.

In particular, since the eye area in the face varies according to the race, error rate rises when the algorithm is applied. When the driver has the low sitting height or shakes his/her head, it gets out of the recognition range of the camera and causes error.

Also in the recognition method using the respiration, the error rate varies according to a location of a sensor which detects the respiration. When air flows from the outside or the driver opens or closes a window, it can greatly affect the sensor.

To implement an intelligent vehicle, it is quite important to obtain the state of the driver in the vehicle or a driving propensity of the driver and to send this information to other vehicle or a host system.

An accident rate caused by the drowsy driving due to fatigue or monotonousness of the driver, or the lack of oxygen inside the automobile tends to increase. Hence, to realize an intelligent automobile system for protecting the driver against the accident caused by the drowsy driving, it is necessary to develop a more effective drowsiness preventing system.

SUMMARY OF THE INVENTION

To address the above-discussed deficiencies of the prior art, it is a primary aspect of the present invention to provide a system and a method for measuring user's brainwaves without contact and preventing user's drowsiness based on a drowsy state determined based on the measured brainwaves.

According to one aspect of the present invention, a system for preventing drowsiness includes a receiver for receiving a signal around a head of a user without contact; a calculator for calculating brainwaves of the user using the signal received at the receiver; and a processor for detecting a state of the user based on the brainwaves of the user calculated by the calculator, and performing a necessary function according to the detected state of the user.

The receiver may include a first receiver for receiving the brainwaves of the user together with noise; and a second receiver for receiving the noise. The calculator may calculate the brainwaves of the user by removing a reception result of the second receiver from a reception result of the first receiver.

The first receiver and the second receiver may include a plurality of contactless electrodes.

The plurality of the contactless electrodes in the first receiver and the second receiver may be arranged in a particular pattern.

The first receiver may be disposed in a central area, and the second receiver is disposed in a lateral area.

The calculator may apply Near Field Super-Directivity (NFSD) gain processing to the reception result of the first receiver and the reception result of the second receiver respectively, and then remove the reception result of the second receiver from the reception result of the first receiver.

The user may be a driver, and the state of the user may be a drowsy state of the user.

According to another aspect of the present invention, a method for preventing drowsiness includes receiving a signal around a head of a user without contact; calculating brainwaves of the user using the signal received in the receiving operation; detecting a state of the user based on the brainwaves of the user calculated in the calculating operation; and performing a necessary function according to the state of the user detected in the detecting operation.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other aspects, features, and advantages of certain exemplary embodiments of the present invention will be more apparent from the following description taken in conjunction with the accompanying drawings, in which:

FIG. 3 is a diagram of actual signals for calculating the driver's brainwaves by removing lateral signals NFSD-gain-processed from a central signal NFSD-gain-processed;

FIG. 4 is an internal block diagram of the drowsy driving preventing system of FIG. 1;

FIG. 5 is a flowchart of a drowsy driving preventing method according to an exemplary embodiment of the present invention;

FIG. 6 is a table of user's mental and physical states according to a frequency of the brainwaves.

Throughout the drawings, like reference numerals will be understood to refer to like parts, components and structures.

DETAILED DESCRIPTION OF THE INVENTION

The following description with reference to the accompanying drawings is provided to assist in a comprehensive understanding of exemplary embodiments of the invention as defined by the claims and their equivalents.

Figure 1:
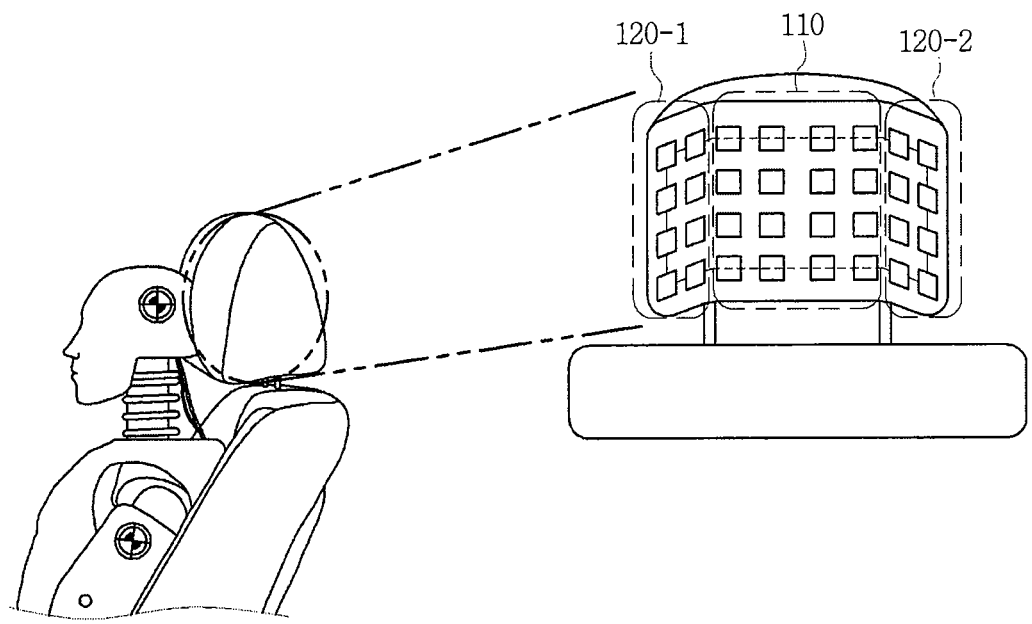
FIG. 1 is a diagram of an exterior of a drowsy driving preventing system according to an exemplary embodiment of the present invention.

FIG. 1 depicts an exterior of a drowsy driving preventing system according to an exemplary embodiment of the present invention. The drowsy driving preventing system is a system which detects driver's brainwaves using contactless electrodes without contact, obtains the drowsy state of the driver based on the detected brainwaves, and calls driver's attention by generating an alarm if necessary.

As shown in FIG. 1, on or in a surface of a head rest of a driver's seat, contactless electrodes which are components of the drowsy driving preventing system are disposed. The contactless electrodes are divided into three groups in FIG. 1.

That is, the contactless electrodes of the drowsy driving preventing system are grouped to:

1) a central electrode array 110 arranged in the center of a head rest area, 2) a right electrode array 120-1 arranged in the right side of the head rest area, and 3) a left electrode array 120-2 arranged in the left side of the head rest area.

The central electrode array 110 arranges the contactless electrodes in a 4×4 pattern, and the right electrode array 120-1 and the left electrode array 120-2 arrange the contactless electrodes in a 2×4 pattern.

All of the central electrode array 110 and the lateral electrode arrays 120-1 and 120-2 are disposed around the driver's head. The central electrode array 110 is relatively close to a brainwave generation point (the center region of the back of the driver's head) of the driver head, whereas the lateral electrode arrays 120-1 and 120-2 are relatively away from the brainwave generation point of the driver head.

Signals received/collected through the central electrode array 110 and signals received/collected through the lateral electrode arrays 120-1 and 120-2 are used to calculate the brainwaves of the driver.

Figure 2:
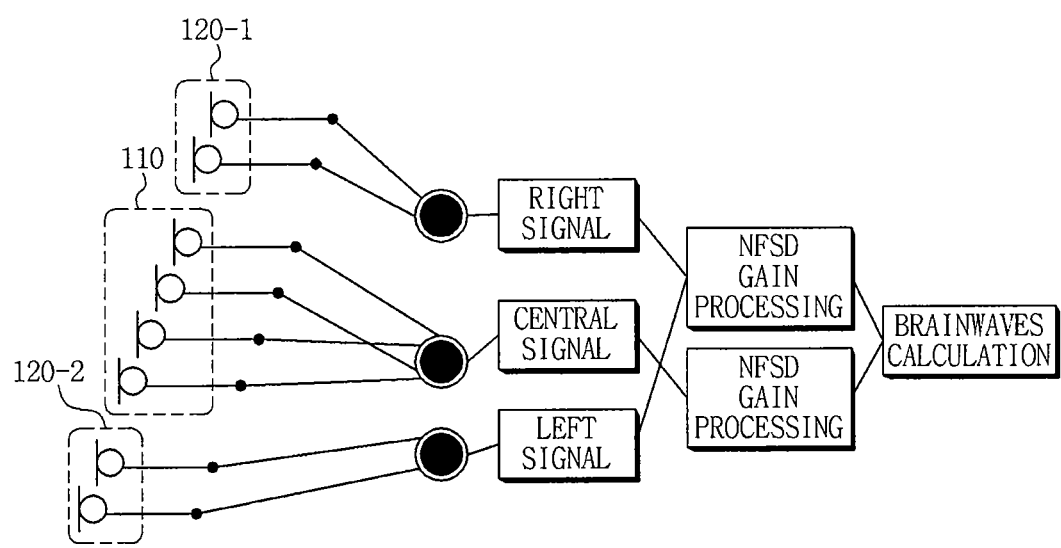
FIG. 2 is a diagram of driver brainwave calculation in the drowsy driving preventing system according to an exemplary embodiment of the present invention.

Hereafter, the calculation of the driver's brainwave in the drowsy driving preventing system is explained in detail by referring to FIG. 2. FIG. 2 shows the driver brainwave calculation in the drowsy driving preventing system according to an exemplary embodiment of the present invention.

Referring to FIG. 2, 1) signals received through the central electrode array 110 are collected as central signals, 2-1) signals received through the right electrode array 120-1 are collected as right signals, and 2-2) signals received through the left electrode array 120-2 are collected as left signals.

The central signal passes through Near Field Super-Directivity (NFSD) gain processing, and the right signal and the right signal are combined and NFSD-gain-processed.

The NFSD-gain-processing deals with the driver's head which is the close signal source, as the main signal source according to a near field scheme, and processes the signal by considering a beamforming gain together with directivity according to a super-directivity scheme.

Next, using the NFSD-gain-processed central signal and the NFSD-gain-processed lateral signals, the brainwaves of the driver are calculated. The NFSD-gain-processed central signal combines the driver's brainwave signal and an ambient noise signal, whereas the NFSD-gain-processed lateral signals include merely the ambient noise signal.

Thus, the driver's brainwaves can be calculated by removing the NFSD-gain-processed lateral signals from the NFSD-gain-processed central signal. In FIG. 3, a method for calculating the driver's brainwaves by removing the NFSD-gain-processed lateral signals from the NFSD-gain-processed central signal is illustrated with the actual signals.

Hereafter, an internal structure of the drowsy driving preventing system of FIG. 1 is elucidated by referring to FIG. 4. FIG. 4 is an internal block diagram of the drowsy driving preventing system of FIG. 1.

As shown in FIG. 4, the drowsy driving preventing system includes the electrode arrays 110, 120-1, and 120-2, signals amplifiers 131, 132-1, and 132-2, signals collectors 141, 142-1, and 142-2, NFSD gain processors 151 and 152, a brainwave calculator 160, a drowsy state detector 170, and an warning generator 180.

The central electrode array 110 is the group of the contactless electrodes arranged in the center area of the head rest, and collects signals at a point relatively close to the brainwave generation point of the driver head.

The central signal amplifier 131 amplifies the signals received from the contactless electrodes of the central electrode array 110, and the central signal collector 141 collects and outputs the signals amplified by the central signal amplifier 131, as the central signal.

The right electrode array 120-1 is the group of the contactless electrodes arranged in the right area of the head rest, and collects signals at a point relatively far away from the brainwave generation point of the driver head.

The right signal amplifier 132-1 amplifies the signals received from the contactless electrodes of the right electrode array 120-1, and the right signal collector 142-1 collects and outputs the signals amplified by the right signal amplifier 132-1, as the right signal.

The left electrode array 120-2 is the group of the contactless electrodes arranged in the left area of the head rest, and collects signals at a point relatively far away from the brainwave generation point of the driver head.

The left signal amplifier 132-2 amplifies the signals received from the contactless electrodes of the left electrode array 120-2, and the left signal collector 142-2 collects and outputs the signals amplified by the left signal amplifier 132-2, as the left signal.

The central signal NFSD gain processor 151 applies the NFSD gain processing to the central signal output from the central signal collector 141.

The lateral signal NFSD gain processor 152 combines the right signal output from the right signal collector 142-1 and the left signal output from the left signal collector 142-2, as the lateral signal and applies the NFSD gain processing to the lateral signal.

The brainwave calculator 160 outputs the brainwave signal by removing the lateral signal NFSD-gain-processed by the lateral signal NFSD gain processor 152 from the central signal NFSD-gain-processed by the central signal NFSD gain processor 151.

The drowsy state detector 170 detects the drowsy state of the driver by analyzing the brainwave signal calculated by the brainwave calculator 160.

The warning generator 180 determines whether the warning is necessary, based on the drowsy state of the driver detected by the drowsy state detector 170. When the warning is necessary, the warning generator 180 calls the driver's attention by generating the warning.

The generated warning can be at least one of auditory information such as sound, visual information such as warning light, and tactile information for vibrating the driver seat or the steering wheel.

Now, a method for preventing the drowsy driving of the driver through the drowsy driving preventing system of FIG. 1 is explained in detail by referring to FIG. 5. FIG. 5 is a flowchart of the drowsy driving preventing method according to an exemplary embodiment of the present invention.

As shown in FIG. 5, firstly, the signals collected by the central electrode array 110 at the point relatively close to the brainwave generation point of the driver head are amplified by the central signal amplifier 131 and then gathered by the central signal collector 141 (S210).

The signals collected by the lateral electrode arrays 120-1 and 120-2 at the points relatively away from the brainwave generation point of the driver head are amplified by the lateral signal amplifiers 132-1 and 132-2, and then gathered by the lateral signal collectors 142-1 and 142-2 (S220).

The central signal NFSD gain processor 151 applies the NFSD gain processing to the central signal collected in step S210 (S230), and the lateral signal NFSD gain processor 152 combines the lateral signals collected in step S220 and applies the NFSD gain processing (S240).

Next, the brainwave calculator 160 calculates the brainwave signal by removing the lateral signals NFSD-gain-processed in step S240 from the central signal NFSD-gain-processed in step S230 (S250).

The drowsy state detector 170 detects the drowsy state of the driver by analyzing the brainwave signal calculated in step S250 (S260). The drowsy state can be detected in step S260 based on a table of FIG. 6. FIG. 6 shows the table of driver's mental and physical states according to a frequency of the brainwaves.

According to the drowsy state of the driver detected in step S260, the warning generator 180 generates the warning if necessary (S270).

Figure 7:
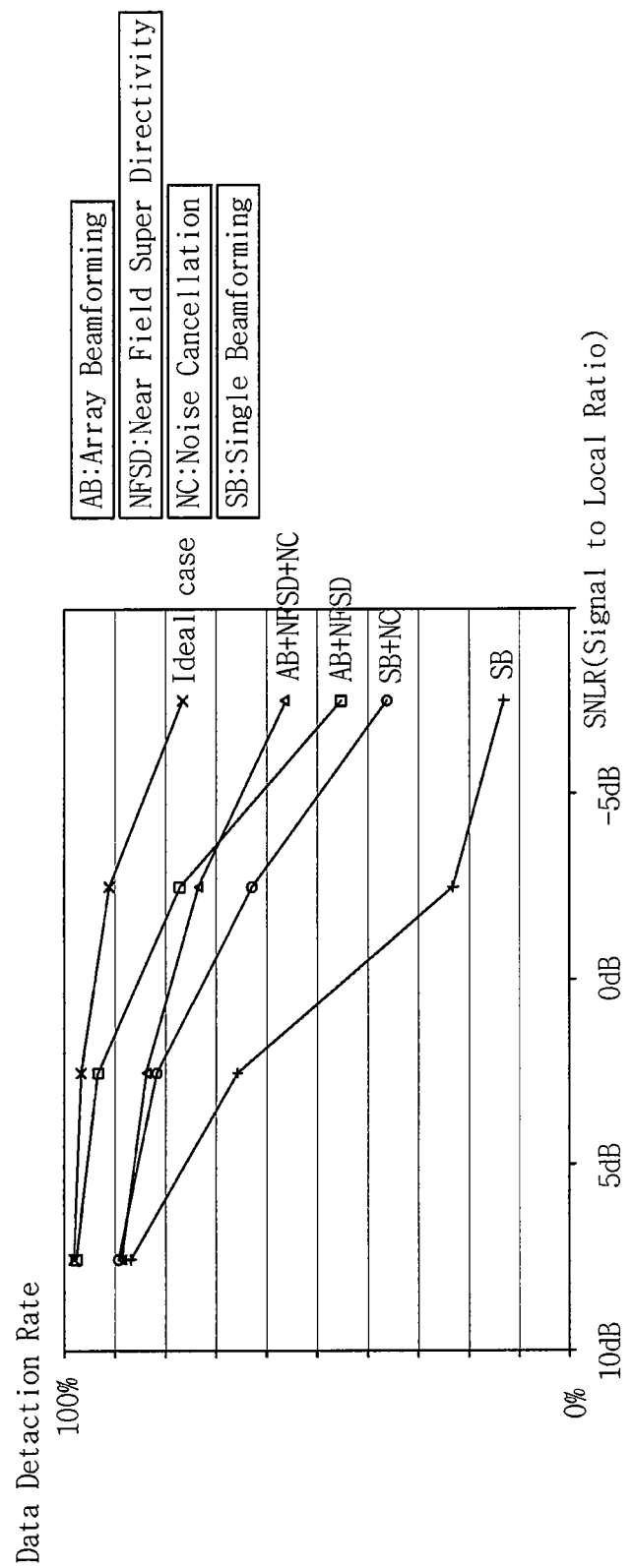
FIG. 7 is a diagram of simulation results of the drowsy driving preventing system according to an exemplary embodiment of the present invention.

FIG. 7 is a diagram of simulation results of the drowsy driving preventing system according to an exemplary embodiment of the present invention. In FIG. 7, 1) "SB" is the simulation result in a system using a single electrode, rather than arraying the contactless electrodes, 2) "SB+NC" is the simulation result of a system using a single electrode by adopting a noise removing scheme, 3) "AB+NFSD" is the simulation result of a system which arraying the contactless electrodes and applies the NFSD gain processing, 4) "AB+NFSD+NC" is the simulation result of a system which arrays the contactless electrodes, applies the NFSD gain processing, and then removes noise, and 5) "Ideal case" is the theoretical ideal result of the system.

As shown in FIG. 7, the system which arrays the contactless electrodes, applies the NFSD gain processing, and then removes noise exhibits the better performance than the system using the single electrode.

Also, the performance is enhanced even by conducting at least one of the arrangement of the contactless electrode array, the NFSD gain processing, and the noise removing.

So far, the drowsy driving preventing system and method have been described in detail with the exemplary embodiments of the present invention.

In the above embodiments, the arrangement pattern of the contactless electrodes is merely exemplary to ease the understanding. It is noted that the contactless electrodes can be arranged in some other pattern than the exemplary pattern, and that the number and the location of the electrodes of the array can be changed according to the size of the head rest and the internal size of the automobile.

In the above embodiments, the drowsy state of the driver is detected, for example, based on the brainwaves to ease the understanding. The present invention can be also applied to detect some other state than the drowsy state of the user based on the user's brainwaves.

As stated above, according to the present invention, the convenience is increased when measuring the brainwaves of the driver using the contactless electrodes. Also, the brainwaves can be accurately detected by arraying the contactless electrodes.

In addition, by detecting and removing the noise received/collected together with the brainwaves, the brainwaves can be calculated more accurately and ultimately the error of the inaccurate user state detection can be reduced.

While the invention has been shown and described with reference to certain exemplary embodiments thereof, it will be understood by those skilled in the art that various changes in form and details may be made therein without departing from the spirit and scope of the invention as defined by the appended claims and their equivalents.

What is claimed is:

1. A system for preventing drowsiness, comprising:
a first receiver configured to receive a first signal comprising brainwaves from a head of a user together with noise, without contacting the user's head;
a second receiver configured to receive a second signal comprising the noise;
a calculator configured to calculate brainwaves of the user using the first and second signals; and
a processor configured to detect a state of the user based on the calculated brainwaves of the user, and to perform a function according to the detected state of the user,
wherein the calculator applies Near Field Super-Directivity (NFSD) gain processing to the first signal and the second signal respectively, and then removes the second signal from the first signal.

2. The system of claim 1, wherein:
the calculator calculates the brainwaves of the user by removing the second signal from the first signal.

3. The system of claim 2, wherein the first receiver and the second receiver comprise a plurality of contactless electrodes.

4. The system of claim 3, wherein the plurality of the contactless electrodes in the first receiver and the second receiver is arranged in a particular pattern.

5. The system of claim 3, wherein the first receiver is disposed in a central area, and the second receiver is disposed in a lateral area.

6. The system of claim 1, wherein the user is a driver, and the state of the user is a drowsy state of the user.

7. A method for preventing drowsiness, comprising:
receiving a first signal comprising brainwaves from a head of a user together with noise, without contacting the user's head;
receiving a second signal comprising the noise;
calculating brainwaves of the user using the first and second signals;
detecting a state of the user based on the calculated brainwaves of the user; and
performing a function according to the state of the user detected in the detecting operation,
wherein the calculating comprises Near Field Super-Directivity (NFSD) gain processing the first signal and the second signal respectively, and then removing the second signal from the first signal.

8. The system of claim 1, wherein the first and second receivers are positioned in a headrest.

9. The system of claim 6, further comprising:
a warning generator configured to generate a warning when the state of the user is the drowsy state.

* * * * *